United States Patent [19]

Stewart et al.

[11] Patent Number: 5,834,431

[45] Date of Patent: Nov. 10, 1998

[54] DES-ARG⁹-BK ANTAGONISTS

[75] Inventors: John M. Stewart, Denver; Eric T. Whalley, Golden; Lajos Gera, Denver, all of Colo.

[73] Assignees: Cortech, Inc., Denver; University of Colorado, Boulder, both of Colo.

[21] Appl. No.: 526,764

[22] Filed: Sep. 8, 1995

[51] Int. Cl.$^6$ .......................... A61K 38/00; A61K 38/02; C07K 5/00; C07K 7/00

[52] U.S. Cl. ............................ 514/15; 530/314; 530/327; 530/328

[58] Field of Search ............................... 514/15; 530/314, 530/327, 328

[56] References Cited

FOREIGN PATENT DOCUMENTS 9406453  3/1994  WIPO ............................. A61K 37/02

OTHER PUBLICATIONS

Hu, D.–E., et al., "[Leu$^8$]des–Arg$^9$–Bradykinin Inhibits the Angiogenic Effect of Bradykinin and Interleukin–1 in Rats," *Br. J. Pharmacol.*, 109, 14–17 (1993).

Marceau, F., et al., "Kinin Receptors of the B1 Type and Their Antagonists," In: *Bradykinin Antagonists—Basic and Clinical Research*, Burch, R.M., (ed.), Marcel Dekker, Inc., New York, pp. 33–49 (1991).

*Primary Examiner*—Avis M. Davenport
*Attorney, Agent, or Firm*—Cushman Darby & Cushman IP Group of Pillsbury Madison & Sutro LLP

[57] ABSTRACT

The present invention provides des-Arg$^9$ bradykinin analogs which are selective B1 receptor antagonists.

12 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

```
Xaa  Gly  Lys  Arg  Pro  Pro  Gly  Phe  Ser  Pro  Leu
 1                  5                          1 0
```

DES-ARG⁹-BK ANTAGONISTS

FIELD OF THE INVENTION

The invention relates to novel biologically active peptides which act as antagonists of the biological activities of bradykinin (BK) and related kinins, in particular, desArg$^9$-BK and desArg$^{10}$ kallidin, the pharmaceutically acceptable salts of these antagonists, and their use as therapeutic agents.

BACKGROUND OF THE INVENTION

Bradykinin (BK), a nonapeptide (Arg$^1$-Pro$^2$-Pro$^3$-Gly$^4$-Phe$^5$-Ser$^6$-Pro$^7$-Phe$^8$-Arg$^9$) and its physiologically important related peptides, kallidin (Lys-bradykinin) and Met-Lys-bradykinin, exhibit physiogical actions which qualify them as mediators of inflammatory reactions, hypotensive states, and pain. Bradykinin is overproduced in pathological conditions such as septic shock (Robinson et al., *Am. J Med.* 59: 61 (1975)) and hemorrhagic shock (Hirsch et al., *J Surg. Res.* 17: 147 (1974)), anaphylaxis (Collier and James, *J Physiol.* 160: 15P (1966)), arthritis (Jasani et al., *Ann. Rheum. Dis.* 28: 497 (1969); Hamberg et al., *Agents Actions* 8: 50( 1978); Sharma et al., *Arch. Int. Pharmacodyn.* 262: 279 (1983)), rhinitis (Proud et al., *J Clin. Invest.* 72: 1678 (1983); Naclerio et al., *Clin. Res.* 33: 613A (1985)), asthma (Christiansen et al., *J. Clin. Invest.* 79: 188 (1987)), inflammatory bowel disease (Zeitlin and Smith, *Gut* 14: 133 (1973)), and certain other conditions including acute pancreatitis, post-gastrectomy dumping syndrome, carcinoid syndrome, migraine, and hereditary angioedema (Leme, Handb. Exp. Pharmacol. 50/I: 464 (1978)). The production of bradykinin results in pain at the site of the pathological condition, and the overproduction intensifies the pain directly or via stimulation by bradykinin of the activation of the arachidonic acid pathway which produces prostaglandins and leukotrienes, more distal mediators of inflammation (Handbook of Experimental Pharmacology, Vol. 25, Springer-Verlag (1969), and Vol. 25 Supplement (1979); Stewart, in "Mediators of the Inflammatory Process," Henson and Murphy, eds., Elsevier, (1989)).

Bradykinin has been found to be produced in inflammatory reactions in the intestine, provoking contraction of smooth muscle and secretion of fluid and ions. The existence of specific bradykinin receptors in the mucosal lining of the intestine and in intestinal smooth muscle is demonstrated by Manning et al. (*Nature* 229: 256 (1982)), showing the influence of bradykinin in very low concentrations upon fluid and ion secretion.

The production of bradykinin and associated pain in angina has been studied and reported (Kimura et al., *Amer. Heart J.* 85: 635 (1973); Staszewska-Barczak et al., *Cardiovasc. Res.* 10: 314 (1976)). The reported action of bradykinin and prostaglandins acting in concert are the natural stimulus for excitation of the sensory receptors signalling the pain of myocardial ischemia.

Bradykinin in combination with interleukin-1 has been shown to stimulate angiogenesis in vivo (*Br.J.Pharmaco.* 109:14–17 (1993)).

Bradykinin and bradykinin-related kinins are not only produced endogenously, but may also be injected into an animal via stings or bites. It is known that insects such as hornets and wasps inject bradykinin related peptides that cause pain, swelling and inflammation.

Bradykinin and related peptides exert their actions on biological systems by combining with specific receptors on cell membranes in the affected tisues. These receptors are of two classes, designated B1 and B2. The B2 receptors require the entire bradykinin sequence for effective receptor combination and production of the biological effects, whereas the B1 receptors do not respond to intact bradykinin, but respond selectively to bradykinin lacking the carboxy-terminal arginine residue; designated [des-Arg$^9$]-bradykinin. [des-Arg$^9$]-bradykinin is produced in the body by one of the enzymes that normally destroys bradykinin, the plasma enzyme carboxypeptidase N, which removes the carboxy-terminal arginine residue. Essentially all normal physiological responses and many pathophysiological responses to bradykinin are mediated by B2 receptors, whereas in certain damaged tissues and in certain kinds of chronic inflammation, B1 receptors are induced.

The search for understanding of the mechanisms of action of bradykinin, which is essential for the development of useful tools for diagnostic use, and for the development of therapeutic agents aimed at alleviating the intense pain and other symptoms caused by the overproduction of bradykinin, was severely hindered by the lack of specific sequence-related competitive antagonists of bradykinin until the discovery of the first effective bradykinin antagonists by Vavrek and Stewart in 1985 (Vavrek et al., *Peptides* 6:161–164 (1985); U.S. Pat. No. 4,693,993). In these early antagonists, the proline residue at position 7 of bradykinin was replaced by a D-aromatic amino acid residue, usually D-phenylalanine or D-thienylalanine. Subsequently, many modifications of the original bradykinin antagonists have been described (reviewed by J. M. Stewart and R. J. Vavrek in R. M. Burch, ed., "Bradykinin Antagonists," Pergamon, 1990), but most effective antagonists have had an aromatic amino acid residue at positions 5 and 8 and a D-aromatic residue at position 7. In certain antagonists, positions 5, 7, and 8 are occupied by aliphatic amino acid residues (J. M. Stewart, et al. in "Peptides 1992," C. H. Schneider and A. N. Eberle, eds., ESCOM, Leiden, 1993, pp 691–692).

Several peptide antagonists of BK exhibit selectivity for the B1 receptor. The basic manipulation for obtaining a selective and competitive antagonist for kinins on the B1 receptor systems is to replace the aromatic residue Phe$^8$ in desArg$^9$-BK (or Phe$^9$ in desArg$^{10}$-kallidin (KD)) by an amino acid possessing an aliphatic side chain, Leu being optimal. Thus, [Leu$^8$, des-Arg$^9$]-bradykinin and Lys-[Leu$^8$, des-Arg$^9$]-bradykinin are effective B1 receptor antagonists. However, Ala, Ile, cyclohexylAla, norLeu and D-Leu substitutions also yield B1 antagonists of lower affinity.

[Leu$^8$, des-Arg$^9$]-bradykinin has been shown to inhibit the angiogenic response elicited by bradykinin (Hu et al., *Br. J. Pharmacol.* 109:14–17 (1993)). In contrast, B2 receptor antagonists failed to inhibit this response. Thus, B1 antagonists may prove effective against angiogenic diseases such as rheumatoid arthritis, diabetic retinopathy and cancer. [Leu$^8$, des-Arg$^9$]-bradykinin has also been shown to cause a reduction in type I diabetic hyperglycemia (Zuccollo et al., Proceedings of the Fourteenth International Symposium on Kinins (1995)). Again, B2 receptor antagonists failed to have an effect on hyperglycemia.

However, these B1 antagonists' effectiveness is hindered by their lack of stability and short term of action. Thus, a need exists for potent, stable compounds capable of selectively antagonizing the B1 receptor with long duration of action.

SUMMARY OF THE INVENTION

The present invention provides des-Arg$^9$ bradykinin antagonists (BKA) of the general formula:

X—A⁰—B¹—C²—D³—E⁴—F⁵—G⁶—H⁷—J⁸—Z wherein
X is an aromatic, aliphatic, aromatic-aliphatic, alicyclic, heterocyclic or urethane-type acylating group, or at least one amino acid;
A⁰, B¹, C², D³, and E⁴ are basic or neutral aromatic, aliphatic, heterocyclic, or alicyclic amino acids or A⁰ is absent;
G⁶ is an aromatic, aliphatic, heterocyclic, or alicyclic amino acid;
F⁵, H⁷ and J⁸ are aromatic, aliphatic, aliphatic heterocyclic, or alicyclic amino acids, provided that at least one of F⁵, H⁷ and J⁸ is selected from cyclopentane-, cyclohexane- or indane-substituted glycine; and
Z is COOH.

DETAILED DESCRIPTION OF THE INVENTION

The present invention provides a new class of des-Arg⁹ bradykinin analogs which are highly potent and selective B1 receptor antagonists with longer duration of action and greater stability than prior des-Arg⁹ derivatives. The present invention provides modified bradykinin antagonist peptides that contain amino acids, preferably glycine, substituted on the α-carbon or on the α-nitrogen by 1-indanyl or 2-indanyl groups, or cyclopentyl or cyclohexyl groups. In a preferred embodiment, the bradykinin antagonist peptides of the present invention contain substituted amino acid residues at positions five, seven and eight of the bradykinin native sequence.

The bradykinin antagonist peptides of the present invention may be characterized as follows:

X—A⁰—B¹—C²—D³—E⁴—F⁵—G⁶—H⁷—J⁸—Z

B¹ is Arg or another basic or neutral aromatic, aliphatic, heterocyclic or alicyclic amino acid of the D- or L-configuration,
C² is Pro, Hyp, or another basic or neutral aromatic, aliphatic, heterocyclic, or alicyclic amino acid of the D- or L- configuration,
D³ is Pro, Hyp, or another basic or neutral aromatic, aliphatic, heterocyclic, or alicyclic amino acid of the D- or L- configuration,
E⁴ is Gly, Niga, Nigb or another basic or neutral aromatic, aliphatic, heterocyclic, or alicyclic amino acid of the D- or L- configuration,
F⁵ is Igla, Iglb, Niga, Nigb, Phe, Thi, Cpg, Chg, or another aliphatic, aliphatic heterocyclic, or alicyclic amino acid of the D- or L- configuration,
G⁶ is Ser, Ser(SO₄), HBQ or another aromatic, aliphatic, heterocyclic, or alicyclic amino acid of the D- or L-configuration,
H⁷ is Igla, Iglb, Niga, Nigb, Tic, Cpg, Chg, or another aliphatic, aliphatic heterocyclic, or alicyclic amino acid of the D- or L- configuration,
J⁸ is Igla, Iglb, Niga, Nigb, Tic, Nbn, Oic, Cpg, Chg, Leu or another aromatic, aliphatic, aliphatic heterocyclic, or alicyclic amino acid of the D- or L- configuration, and
Z represents the terminal carboxy group. Where Z is not set forth in the above formula, it is understood to be present.

According to the above formula, X and A may be alternatively described as being optionally absent in which case they may represent the terminal amino group. Where X is present, it is preferably a single amino acid residue or a di-peptide.

The bradykinin antagonist peptides of the present invention may be illustrated by the following (alignment of the residues in a particular row does not imply nor limit to a given peptide sequence):

| X -- | A --<br>0 | B --<br>1 | C --<br>2 | D --<br>3 | E --<br>4 | F --<br>5 | G --<br>6 | H --<br>7 | J<br>8 |
|---|---|---|---|---|---|---|---|---|---|
| Aaa | DArg | Arg | Pro | Hyp | Gly | Igla | Ser | DIgla | Igla |
| Aca | DLys | Lys | DMF | Pop | Iglb | Ser(SO₄) | DIglb | Iglb | Lys |
| Acetyl | Arg | DArg | NMF | Niga | Nigb | Niga | HBQ | Niga | Niga |
| Dhq | Lys | DLys | MPIV | MPIV | Ala | Nigb | Cys | Nigb | Nigb |
| Nba | Gly | Cys | Hyp | Pro | Gly | Leu | Gly | DLeu | Leu |
| Tba | | | Azt | Azt | | Chg | DChg | Chg | NChg |
| Cha | | | Dhp | Dhp | | Ile | DIle | Ile | |
| Cpa | | | Inip | Inip | | Val | DVal | Val | |
| Gun | | | Thz | Thz | | Alg | DCpg | Cpg | |
| | | | Pop | | | Oic | DOic | Oic | |
| | | Lys-Lys | | | | Pop | DPop | Pop | |
| | | | | | | Nle | DNle | Nle | |
| | | | | | | DMF | DDMF | DTic | |
| | | | | | | Cpg | Tic | | |
| | | | | | | Thi | DTic | | | wherein
X is the amino-terminal amino group or an aromatic, aliphatic, aromatic-aliphatic, alicyclic, heterocyclic or urethane-type acylating group, a single amino acid of the D- or L- configuration, or a di- or poly-peptide containing amino acids of the D- or L-configuration, or a combination of these,
A⁰ is D-Arg or another basic or neutral aromatic, aliphatic, heterocyclic or alicyclic amino acid of the D- or L- configuration, In a preferred embodiment, the bradykinin antagonist peptides of the present invention are represented as follows:
X is Gun or absent;
A⁰ is DArg or Lys;
B¹ is Arg or Cys;
C² is Pro;
D³ is Hyp;
E⁴ is Gly;
F⁵ is Igla, Iglb, Cpg or Thi;

$G^6$ is Ser;
$H^7$ is DIgla, DIglb, DCpg, Tic or DTic; and
$J^8$ is Leu, Cpg or Oic.

Preferred embodiments may be represented as follows:

SC-722 DArg-Cys-Pro-Hyp-Gly-Cpg-Ser-DCpg-Cpg
SC-724 DArg-Lys-Pro-Hyp-Gly-Cpg-Ser-DCpg-Cpg
B9004 DArg-Arg-Pro-Hyp-Gly-Cpg-Ser-Tic-Cpg
B9006 DArg-Arg-Pro-Hyp-Gly-Thi-Ser-Tic-Cpg
B9066 DArg-Arg-Pro-Hyp-Gly-Cpg-Ser-DTic-Cpg
B9068 DArg-Arg-Pro-Hyp-Gly-Thi-Ser-DTic-Cpg
B9102 DArg-Arg-Pro-Hyp-Gly-Cpg-Ser-DCpg-Cpg
B9810 Gun-Gly-Lys-Arg-Pro-Pro-Gly-Phe-Ser-Pro-Leu (SEQ ID NO:1)
B9812 DArg-Arg-Pro-Hyp-Gly-Igl-Ser-DIgl-Oic
B9814 Arg-Pro-Hyp-Gly-Igl-Ser-DIgl-Leu
B9816 DArg-Arg-Pro-Hyp-Gly-Igl-Ser-DIgl-Leu
B9822 Gun- DArg-Arg-Pro-Hyp-Gly-Igl-Ser-DIgl-Oic
B9824 DArg-Arg-Pro-Hyp-Gly-Thi-Ser-DIgl-Oic
B9826 Gun- DArg-Arg-Pro-Hyp-Gly-Thi-Ser-DIgl-Oic
B9840 DArg-Arg-Pro-Hyp-Gly-Igl-Ser-DTic-Cpg
B9842 Lys-Arg-Pro-Hyp-Gly-Igl-Ser-DTic-Cpg
B9856 Lys-Arg-Pro-Hyp-Gly-Igl-Ser-DIgl-Oic
B9858 Lys- Lys-Arg-Pro-Hyp-Gly-Igl-Ser-DIgl-Oic
DArg-Arg-Pro-Hyp-Gly-Thi-Ser-DTic-NChg

More preferred embodiments of the present invention are:

Lys-Lys$^0$-Arg$^1$-Pro$^2$-Hyp$^3$-Gly$^4$-Iglb$^5$-Ser$^6$-DIglb$^7$-Oic$^8$; and Gun-DArg$^0$-Arg$^1$-Pro$^2$-Hyp$^3$-Gly$^4$-Thi$^5$-Ser$^6$-DIglb$^7$-Oic$^8$.

According to this invention, the indane substituent can be on either the α-carbon (residues abbreviated Igl) or the nitrogen (residues abbreviated Nig) of the glycine residue, and the indane residue can be attached to the glycine moiety at either position 1 (Igla or Niga) or position 2 (Iglb or Nigb) of the indane group.

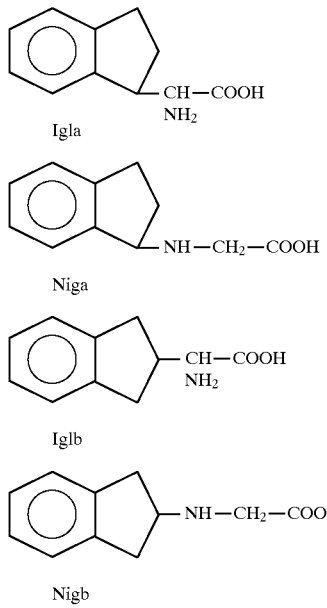

As used herein, abbreviations of the natural amino acids are those accepted in the art (*Biochem. J.* 126: 773 (1972)), and unless prefixed with D are all of the L-configuration (except glycine and MPIV, which are not optically active).

Abbreviations used for unnatural amino acids in Bradykinin analogs are indicated below:

AC6 1-Aminocyclohexane-1-carboxylic acid
Alg Allylglycine
Azt Azetine-2-carboxylic acid (norproline)
CDF p-Chloro-D-Phe
Chg CyclohexylGly (α-Aminocyclohexaneacetic acid)
cLeu 1-Aminocyclopentane-1-carboxylic acid (cycloleucine)
Cpg CyclopentylGly (α-Aminocyclopentaneacetic acid)
Dhp 3,4-Dehydro-Pro
DMF 2,4-Dimethylphenylalanine
Eac 6-Aminohexanoic acid (ε-aminocaproic acid)
FDF p-Fluoro-DPhe
Gun Guanidyl
HBQ N5-(4-hydroxybutyl)-glutamnine
Hig Hexahydroindanylglycine
Hyp trans-4-Hydroxy-Pro
Igla α-(1-indanyl)glycine
Iglb α-(2-indanyl)glycine
Inip Isonipecotic acid (piperidine-4-carboxylic acid)
MDY O-Methyl-DTyr
MPIV 2,4-Methanoproline (2-Azabicyclo-(2,1,1)-hexane-1-carboxylic acid)
Nal β-2-Napthyl-Ala
Niga N-(1-indanyl)glycine
Nigb N-(2-indanyl)glycine
Nle Norleucine
NMF N-Methylphenylalanine
Oic Octahydroindole-2-carboxylic acid
OMT O-Methyl-Tyr
Pal β-3-Pyridyl-Ala
PCF p-Chloro-Phe
Pip Pipecolic acid ("homo-Pro")
Pop trans-4-PropoxyPro
Ser(SO$_4$) Serine-O-sulfate
Suc Succinyl
Thi β-2-Thienyl-Ala
Thz Thiazolidine-4-carboxylic acid
Tic 1,2,3,4-Tetrahydroisoquinoline-3-carboxylic acid As used herein, the term "aromatic" shall mean aryl ($C_6$–$C_{12}$), or heteroaryl, wherein the heteroaryl groups are mono- or bi-cyclic five or six membered rings containing one or more heteroatoms such as oxygen, sulfur or nitrogen in any combination and are optionally substituted with alkyl ($C_1$–$C_4$), alkenyl ($C_1$–$C_4$), halo, cyano, nitro, amino, hydroxy groups and the like.

As used herein, the term "aliphatic" shall mean alkyl ($C_1$–$C_{12}$), alkenyl ($C_1$–$C_{12}$) or alkynyl ($C_1$–$C_{12}$) and heteroalkyl ($C_5$–$C_{12}$) or heteroalkenyl ($C_5$–$C_{12}$).

As used herein, the term "alicyclic" shall mean optionally substituted cycloalkyl ($C_4$–$C_{12}$), optionally containing 1–3 double bonds.

As used herein, the term "heterocyclic" shall mean mono- or bi-cyclic five or six membered rings containing one or more heteroatoms such as oxygen, sulfur or nitrogen in any combination, optionally substituted with alkyl ($C_1$–$C_4$), alkenyl ($C_1$–$C_4$), halo, cyano, nitro, amino, hydroxy groups and the like, and optionally containing 1 to 3 double bonds.

Abbreviations used for acylating groups (as used for "X") are as follows:

Aaa- 1-Adamantaneacetyl-
Ac- Acetyl-
Aca- 1-Adamantanecarbonyl-
Bz- Benzoyl-
Cha- Cyclohexaneacetyl-
Cpa- Cyclopentaneacetyl-
Dca- 2,2-Dicyclohexylacetyl-
Dhq- 2,3-Dehydroquinuclidine-3-carbonyl-
Dpa- 2,2-Diphenylacetyl-
Dpp- 3,3-Diphenylpropionyl-
Nba- Norbornane-2-acetyl-
Nbc- 2-(cis-5-norbornene-endo-3-carbonyl)-
Nbi- cis-5-norbornene-endo-2,3-dicarboximidyl-
Paa- Phenylacetyl-
Pba- 4-Phenylbutyryl-
Ppa- 3-Phenylpropionyl-
Sin- Sinapinyl- (3,5-dimethoxy-4-hydroxycinnamyl-)

The description of peptide synthesis methods uses several abbreviations for standard solvents, reagents and procedures, defined as follows:

BOP Benzotriazolyloxy-tris-(dimethylamino) phosphonium hexafluorophosphate
BuOH n-Butanol
DCC Dicyclohexylcarbodiimide
DCM Dichloromethane
DIC Diisopropylcarbodiimide
DIEA Diisopropylethyl amine
DMF Dimethylformamide
HATU O-(7-azabenzotriazol-1-yl)-1,1,3,3-tetramethyluronium hexafluorophosphate
HOAc Acetic acid
MeOH Methanol
OHMR Hydroxymethylpolystyrene resin for peptide synthesis, 1% crosslinked.
TBTU O-(benzotriazol-1-yl)-1,1,3,3-tetramethyluronium tetrafluoroborate
TEA Triethyl amine
TFA Trifluoroacetic acid The following abbreviations for blocking groups used in synthesis are:
Boc t-Butyloxycarbonyl
Tos p-Toluenesulfonyl
Bzl Benzyl ether The following abbreviations for standard techniques used are:
AAA Amino acid analysis (Stewart & Young p. 108)
CCD Countercurrent distribution (Stewart & Young p. 96)
ELEC Paper electrophoresis (Stewart & Young p. 117)
HPLC High performance liquid chromatography (Stewart & Young, p. 100)
Kaiser test Ninhydrin test for completeness of coupling reactions (Stewart & Young, p. 105)
SPPS Solid phase peptide synthesis
TLC Thin-layer chromatography (Stewart & Young, p. 103)

The synthesis of peptides described herein, including preparation of appropriate amino acid derivatives, their activation and coupling to form peptides and methods for purification of peptides and determination of their purity are included in the general body of knowledge of peptide chemistry, as generally described in Houben-Weyl "Methoden der Organischen Chemie" Vol. 16, parts I & II, (1974) for solution-phase synthesis, and in "Solid Phase Peptide Synthesis" by Stewart and Young (1984) for synthesis by the solid phase method. A chemist skilled in the art of peptide synthesis would be able to synthesize the described peptides by standard solution methods or by manual or automatic solid phase methods.

Therapeutic application of bradykinin antagonists include treatment of traumatic, inflammatory or pathological conditions mediated by bradykinins or their closely related metabolites. These conditions may include treatment of bites, stings, general trauma, head trauma, inflammatory conditions including inflammatory bowel disease, burns, rashes, shock or hypotension associated with sepsis, and pain, especially pain associated with surgical or dental procedures. In addition bradykinin antagonists may be used for the treatment of airway hypersensitivity and inflammation, as well as other symptoms associated with asthma. Bradykinin is recognized as a mitogenic agent and compounds disclosed in this invention have exhibited in vitro activity which may indicate their utility as anti-cancer agents. The compounds of the present invention may also be effective in the treatment of angiogenic diseases such as rheumatoid arthritis, diabetic retinopathy and cancer.

The compounds may be administered topically, or by injection or infusion or as an oral suspension in an appropriate vehicle or as tablets, pills, capsules, caplets or the like. The dosage and manner of administration will be defined by the application of the bradykinin antagonist and can be determined by routine methods of clinical testing to find the optimum dose. These doses are expected to be in the range of 0.001 mg/Kg to 100 mg/Kg of active compound.

The compounds are composed of amino acids which may form salts due to their acidic or basic nature, and any pharmacologically acceptable salt derived from the compounds described in this invention such as hydrochlorides, acetates, phosphates, maleates, citrates, benzoates, salicylates, succinates, ascorbates and the like, are considered an extension of this invention. A common tactic in medicinal chemistry is to modify known drug substances which are peptide based to form esters or amides which exhibit greater bioavailability. Prodrugs derived from the compounds disclosed here are therefore considered an obvious extension of this invention. Methods for designing and preparing prodrugs are described in detail in the medicinal chemical literature.

EXAMPLES

Example I

Peptide Synthesis

General Methods

Synthesis of the bradykinin antagonist peptides of the present invention by solid phase peptide synthesis (SPPS) may be carried out manually (see Stewart & Young) or by use of the Beckman Model 990, Biosearch Model 9500 or other automatic peptide synthesizers. SPPS involves use of certain standard procedures, defined as follows:

Procedure A: DCC coupling reaction: (Described in Stewart & Young, p 76ff). A 2.5-fold excess of Boc-amino acids over peptide-resin is used in the Model 990 synthesizer. Boc-amino acids are activated for coupling with an equimolar amount of DCC. The solvent may be DCM or mixtures of DCM and DMF. Completeness of coupling may be determined by use of the Kaiser reagent.

Procedure B: DIC coupling: In the Model 9500 synthesizer a 6-fold excess of Boc-amino acids over peptide-resin is used with an equimolar amount of DIC. The solvent is DCM:DMF (1:1). The resin is washed with the same solvent before and after coupling. Completeness of coupling is determined with the Kaiser reagent.

Procedure C: BOP, TBTU or HATU coupling reaction for hindered amino acids: A 3-fold excess of Boc-amino acid over peptide-resin is mixed with an equimolar amount of BOP, TBTU or HATU and 2 equivalents of DIEA in DMF. The peptide-resin is washed with DMF before and after the coupling reaction, and after coupling is then washed 2 times with methanol before continuing standard DCM washes. Completeness of coupling is checked by the Kaiser test. BOP, TBTU and HATU, in this order, show increasing ability to cause successful coupling of sterically hindered amino acids.

Procedure D: TFA deprotection and neutralization: (Stewart & Young p. 76). The deprotection reagent is TFA:DCM (1:3), containing 1 mg/ml indole. It is used for 30 minutes, following a prewash. The neutralization reagent is 10% TEA in DCM, prepared fresh and used twice for one minute.

Procedure E: Terminal deprotection: (Described by Stewart & Young, p. 79). Deprotection with TFA:DCM is carried out as described in Procedure D. The peptide-resin is then washed three times with DCM and three times with MeOH and dried.

Procedure F: HF cleavage and deblocking: (Stewart & Young p. 85). A batch of 500 mg (0.2 mmole) of peptide-resin is mixed with 1.0 ml anisole and chilled in the reaction vessel to −78° C. and 10 ml of anhydrous HF is distilled into the vessel under vacuum. The mixture is stirred at 0° C. for 45 min, and the HF is evaporated under vacuum. The peptide and resin mixture is washed three times with dry ether, and the peptide is extracted into glacial HOAc. The peptide soluiton is lyophilized.

Procedure G: PURIFICATION OF PEPTIDES: (Stewart & Young p. 96). The peptides may be purified by CCD for 100 transfers in the appropriate system, as determined by preliminary k estimation. Examples of CCD systems are:

A: n-BuOH:1% TFA for average antagonist peptides
B: n-BuOH:ethyl acetate:1% TFA (1:1:2) for more hydrophobic antagonist peptides.
Procedure H: TLC: TLC may be carried out on silica gel plates with systems F (n-BuOH:HOAc:$H_2$O:pyridine= 15:3:8:10) and I (n-BuOH:HOAc:$H_2$O=4:1:1). Chlorine-tolidine and Sakaguchi spray reagents may be used.
Procedure J: Paper electrophoresis (ELEC): ELEC may be done in buffers of pH 2.8 and 5.0 as described in Stewart & Young. Chlorine-tolidine and Sakaguchi spray reagents may be used.
Procedure K: HPLC: Preparative HPLC may be carried out on large-pore reversed phase C4 or C8 silica columns in a gradient of 0.1% TFA in $H_2$O to 0.08% TFA in acetonitrile. Detection may be by UV at 214 or 235 nm. Analytical HPLC may be carried out in the same system and in a gradient of acetonitrile in 0.25M triethylammonium phosphate, pH 6.5.

Procedure L: MASS spectroscopy: Peptides may be checked for the correct molecular mass by fast atom bombardment (FAB) or laser desorption (MALDI) mass spectroscopy.

Procedure M: Amino acid analysis (AAA): Peptides may be hydrolyzed in 6N HCl and analyzed as described in Stewart & Young, pp 109–112, using a Beckman Model 6300 amino acid analyzer.

Example II

Synthesis of des-Arg9-BK Antagonists

Esterification of N-Boc-protected unusual amino acids (cyclopentaneglycine or octahydro-indole-2-carboxylic acid) to the chloromethyl resin was achieved easily without racemization by means of their cesium salts using the standard procedure (Stewart et al., Solid Phase Peptide Synthesis, 2nd ed. Pierce Chemical Company: Rockford, Ill., 1984; pp. 85–88).

A. Cesium Salts of Boc-amino Acids: A solution of Boc-protected unusual amino acid (Boc-cyclopentaneglycine or Boc-octa-hydroindole-2-carboxylic acid) (0.475 mmol) in methanol (20 ml) and water (2ml) was titrated to ph 7 with 20% aqueous cesium carbonate. The solution was evaporated to dryness in vacuo. The residual protected amino acid cesium salt was dried by addition of DMF and re-evaporation two or three times at 45 C. They were dried over P205 for 5 h.

B. Attachment of Boc-amino acid cesium salts to chloromethyl resin: 0.44 mmol of dry Boc-cyclopentaneglycine or Boc-octahydroindole-2-carboxylic acid cesium salt and 1 g (0.4 mmol) of chloromethyl resin in anhydrous DMF (15 ml) were stirred at 50=BO C for 15–24 h. The resin was filtered and washed with DMF, DMF: H20 (1:1), DMF, MeOH and DCM by the standard procedure.

The desired peptide sequences were assembled on the above amino acid-resins using standard procedures, to give potent [des-arg9]-bradykinin analogs BSH=3D Bissuccinimidohexane
Mosi=3D Methoxy-suberimido
Sub =3D Suberyl
Suc =3D Succinyl
Suim =3D Suberinidyl

EXAMPLE III

Synthesis of α-(2-indane)-glycine (IgIb)

2-Bromoindane: To 2-indanol (Aldrich) (105 g, 0.78 mol) in pyridine (16 mL, 0.2 mol) and 340 mL of chloroform at −15° C. was added $PBr_3$ (84 mL, 0.89 mol) over 45 min. The reaction mixture was stirred overnight at room temperature and extracted by addition of 450 mL of chloroform and 500 g of ice. The organic layer was washed twice with water, and dried over $Na_2SO_4$. The solvent was evaporated in vacuo, leaving a brown semi-solid. The product was distilled rapidly in vacuo and then fractionated to give 69 g (45%) 2-bromoindane, bp 90°–93°/3 mmHg; $n_D^{23}$=1.5837.

Ethylα-acetamido-α-cyano-2-indaneacetate: To sodium ethoxide (20.4 g, 0.3 mol), suspended in dry DMSO (250 mL) was added a solution of ethyl acetamidocyanoacetate (50 g, 0.294 mol) in 250 mL dry DMSO, with vigorous stirring. Then 2-bromoindane (65.0 g, 0.33 mol) was added dropwise during 40 min, with vigorous stirring. The brown solution was stirred overnight at room temperature and 4 h at 50° C. The mixture was evaporated in vacuo and the residue was treated with 300 mL cold water and extracted twice with 250 mL of EtOAc. The combined extracts were dried (MgSO$_4$) and evaporated to give the crude product, 70.7 g brown solid. The first recrystallization from EtOH/H$_2$O gave 58.6 g yellowish solid, mp 153°–157°. The second recrystallization from toluene gave 54.6 g (64.9%) white flakes, mp 159°–161° C.

D,L-2-indaneglycine: A solution of 54.6 g (0.19 mol) ethyl α-acetamido-α-cyano-2-indaneacetate in 820 mL of 10% NaOH was refluxed for 20 h. The solution was cooled, decolorized with carbon, and the filtrate, in an ice bath, was adjusted to pH 6.5 with conc. HCl (about 150 mL), using a pH meter, and further chilled to complete precipitation of the product, which was filtered and washed with cold water, methanol and ether; 36.4 g. The solid was refluxed in 1200 miL 6N HCl for 10 h; the solution was decolorized with carbon and chilled to give a precipitate, which was collected and recrystallized from H$_2$O to give 22.6 g product. Additional product was obtained from the mother liquor to give 31.7 g (86.9%) of D,L-2-indaneglycine.

N-acetyl-D,L-2-indaneglycine: To a mixture of 6.83 g (0.03 mol) of D,L-2-indaneglycine and 54 mL H$_2$O was added 30 mL (0.06 mol) 2N NaOH. The solution was chilled and stirred while 1.4 mL (0.015 mol) acetic anhydride was added. Seven successive additions of 2N NaOH (14 mL) and 1.4 mL of acetic anhydride were done over 30 min, and the solution was allowed to warm to room temperature, with continued stirring. Stirring was continued overnight. The solution was chilled and acidified to pH 3 with 6N H$_2$SO$_4$ (40 mL). After standing in the cold, the precipitate was collected and washed with a small amount of cold H$_2$O; 7.95 g, mp 199°–202°. The product was recrystallized from acetone/petroleum ether (30°–60°) to give 7.8 g acetyl D,L-2-indaneglycine, mp 201°–203°.

Resolution of D,L-2-indaneglycine: N-acetyl-D,L-2-indaneglycine (7.0 g, 0.03 mol) was suspended in 300 mL H$_2$O, and the pH was adjusted to 7.6 with 4N LiOH (9 mL). Water was added to a volume of 350 mL, the solution was thermostatted at 37° C., with stirring, and hog kidney acylase I (Sigma A-3010, 50 mg) was added. The pH was maintained at 7.6 by addition of LiOH; after precipitation of L-indaneglycine began, the pH rose and was brought back with 0.1N HOAc. After 5 h an additional 30 mg acylase I was added, and after 24 h an additional 20 mg acylase was added, with continued pH control. Incubation, with stirring was for a total of 36 h. The solution was cooled to room temperature, and 250 mL cold water and 500 mL EtOAc were added. The mixture was carefully acidified to pH 0.75 with 6N HCl (about 25 mL). The two layers were wet filtered through Celite and separated. The water phase was extracted twice with EtOAc (250 mL).

The aqueous solution was decolorized with carbon at 50° and evaporated under reduced pressure. The crystals were dissolved in 25 mL H$_2$O and 25 mL 6N HCl and the cold solution was brought to pH 5.5 with conc. NH$_4$OH. The product was collected, washed with cold water, and dried;
2.8 g (97.6%) L-2-indaneglycine; mp 302°–305°; $[a]_D^{25}$=+35.4° (c 2, 2N HCl).

The ethyl acetate phase was washed with saturated NaCl solution, dried over MgSO$_4$ and evaporated in vacuo. The solid residue was recrystallized from EtOH/petroleum ether to give 3.1 g (88.6%) acetyl-D-2-indaneglycine, mp 210°–212°; $[a]_D^{25}$=−38.7° (c 2, EtOH).

Acetyl D-2-indaneglycine (2.92 g, 0.0125 mol) was refluxed in 125 miL of 6N HCl for 8 H. The solution was evaporated under reduced pressure at 40°, and the residue was dissolved in 40 mL 6N HCl and 150 mL H$_2$O. The solution was neutralized to pH 5.5 with conc. NH$_4$OH, and the white solid was collected, washed with cold water and dried in vacuo to yield 2.17 g (90.8%) of D-2-indaneglycine; mp 302°–305°; $[a]_D^{23}$=−34.6° (c 2, 2N HCl).

Both the D- and L-isomers were converted to the N-Boc derivative by the standard procedure (see the following Example).

EXAMPLE IV

Synthesis of N-Boc-N-(2-indanyl) Glycine(Boc-Nigb)

Synthesis of N-(2-indanyl)-glycine (Nigb): Glycine methyl ester (3.49 g, 0.025 mole) and 2-indanone (4.96 g, 0.0375 mole) were dissolved in EtOH and then NaCNBH$_3$ (4.71 g, 0.075 mole) was added portionwise during about 30 min. The mixture was stirred at room temperature for 24 h. The EtOH was removed under reduced pressure and the residue was treated with water. The product was extracted by several extractions with EtOAc. The organic phase was washed with saturated aqueous NaHCO$_3$, dried over Na$_2$SO$_4$ and evaporated. The product was purified by chromatography over silica gel (EtOAc and EtOAc/MeOH=9:1) to give the crude ester as a colorless oil (2.46 g). The ester (2.43 g in 30 mL MeOH) was saponified with 15 mL 1N NaOH at room temperature for 5h. The solution was concentrated and the residue was taken up in dioxane-water.

Synthesis of the Boc-derivative: The solution was cooled to 0° and treated with Boc anhydride (3.27 g, 0.015 mole) portionwise. The ice bath was removed, and the mixture was stirred overnight at room temperature, with adjustment of pH to 9.0 with NaOH solution as needed. The solution was evaporated to dryness under reduced pressure, the residue was taken up in EtOAc/water (70/30 mL), and the solution was treated with saturated aqueous citric acid solution to pH 2.5. The phases were separated and the water was extracted twice with EtOAc. The organic phase was washed with water, saturated NaCl soution, dried over Na$_2$SO$_4$ and evaporated under reduced pressure. The crude product was recrystallized from EtOAc/hexanes; 1.85 g (25.4%), mp 130°–131° C.

EXAMPLE V

Binding Assays

Human lung fibroblasts IMR-90 cells were obtained from ATCC and propagated in DMEM media in 850 mm roller bottles until confluent. Three hours prior to harvesting, the cells were treated with Interleukin lb (200 pg/ml). Human BK2 clones were propagated in F12 media until confluent.

Preparation of membranes for binding assays was carried out by scraping cells from roller bottles in ice cold PBS and centrifuging at 1000 ×g, at 4° C. for 15 minutes. The supernatant was discarded and pellet resuspended in Buffer A consisting of 25 mM TES(pH 6.8) with 2 uM 1,10-Phenanthroline, and centrifuged at 27,000 ×g for 15 min. this was then repeated. The final pellet was resuspended in Buffer B (Buffer A with 2 uM Captopril, 140 ug/Ml Bacitracin, 0.1%BSA), and stored in 1 ml aliquots, frozen at −20° C. until needed.

Binding assays were performed by incubating human clone membranes with 0.3 nM $^3$H-Bradykinin or IMR-90 membranes with 0.5 nM $^3$H-des-Arg$^9$-Kallidin in the presence of the peptides in assay buffer (Buffer B with 1 mM Dithiotreitol), at room temperature, for 45 minutes. All test compound dilutions were in triplicate. Assays were harvested by quick filtration in a Tomtec Harvester 96, with ice cold wash buffer consisting of 10 mM Tris/HCl, pH 7.5, 100 mM NaCl, 0.02%BSA, onto Wallec printed glassfiber Filtermat "B", which had been pre-soaked with 0.1% PEI and previously air-dried. Filtermats were counted in 9.5 mls Wallec Beta-Plate Scint, in Wallec 1450 MicroBeta Counter.

TABLE I

Binding Data

| Bradykinin Antagonists (desArg9) | Human Binding - pIC$_{50}$ | | GPI Binding - pIC$_{50}$ |
|---|---|---|---|
| | B1 | B2 | B2 |
| B9004(17-27) | 8.5 | 5.8 | 5.2 |
| B9006(13-23) | 7.9 | 6.2 | 5.0 |
| B9066(74-86) | 9.3 | 5.9 | 5.6 |
| B9068(74-84) | 8.8 | 5.7 | 5.1 |
| B9810(15-27) | 8.9 | i.a | i.a |
| B9812(HPLC) | 9.5 | 7.6 | 6.5 |
| B9814(HPLC) | 8.2 | i.a | i.a |
| B9816(HPLC) | 8.9 | 6.2 | 5.7 |
| B9822(HPLC) | 9.0 | 7.1 | 6 |
| B9824(HPLC) | 9.6 | 7.8 | 6.7 |
| B9826(HPLC) | 9.9 | 8.1 | 7.1 |
| B9840(HPLC) | 9.1 | 6.2 | i.a |
| B9842(HPLC) | 9.6 | 6.2 | i.a. |
| B9856(HPLC) | 9.6 | 7.6 | 6.3 |
| B9858(HPLC) | 10.1 | 7.7 | 6.9 | i.a. = inactive. pIC$_{50}$ = −log of the IC$_{50}$ (concentration in molar which inhibits tritiated ligand binding by 50%).

EXAMPLE VI

In Vivo

Mongrel dogs of either sex, weight range 10–15 kg were used. These were anaesthesized with pentobarbitone, 30 mg/kg i.v. and catheters placed in one femoral artery and both femoral veins for the recording of blood pressure and infusion and injection of compounds. Rresponses to (50 nM) were produced in the absence and presence of antagonist and the ED$_{50}$ calculated. After the end of the infusion of the highest dose of the antagonist compound, BK and des-Arg$^9$-BK were injected at intervals for up to four hours.

TABLE II

In vivo B2/B1 Data

| | | BK1 ED$_{50}$ µg/kg/min | Selectivity (BK, desArg9BK, ACh, NE, Sp, AII) | Duration of Action (following 20 min of highest dose) |
|---|---|---|---|---|
| CP-0298 | desArg9 Lys0 Leu8 BX | 0.546 ± .16 (558 pmol) | BK1 at 3.0 µg/kg/min | Almost 100% returned by 15–30 min |
| B9812 | | 0.02 ± 0.003 (10.7 pmol) | B1 only at 1.0 | B1 still 100% blocked at 4.6 h |
| B9858 | | 0.03 ± 0.01 | B1 only at 1.0 | 1.0 µg/kg/min ≧ 50% returned at 4.5 h 0.3 µg/kg/min 100% returned at 3.5–4 h |

ED$_{50}$ = dose of antagonist to inhibit hypotensive response to desArg9BK by 50%.

EXAMPLE VII

Rat Kidney Brush Border Microvilli

Kidney membranes were prepared as indicated in the literature (Booth et al., *Biochemical Journal*, 142: 575 (1974)). Rat kidneys were obtained after sacrifice and rinsed in several volumes of a 2 mM tris, 10 mM mannitol buffer, pH 7.1. Cortical material was carefully removed and homogenized in ten volumes of the buffer. The homogenate was spun in a IEC Centra-8 refrigerated centrifuge. (4° C., 200×g). The supernatant was made 10 mM with respect to MgCl$_2$. The supernatant material was subjected to further centrifugation as indicated:

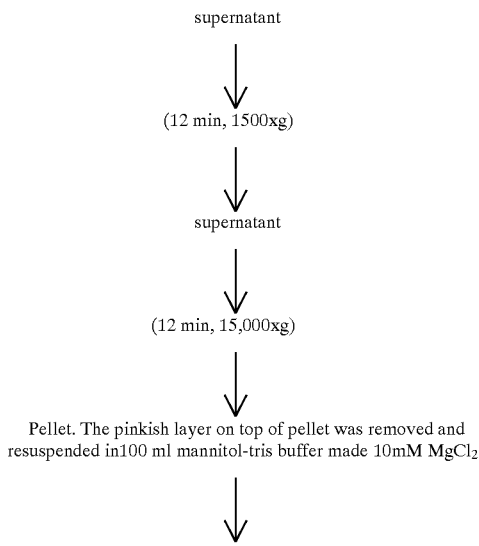

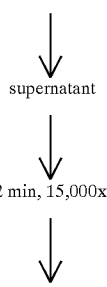

Pellet resuspended in tris-mannitol buffer. Protein concentration was determined by the method of Bradford (*Anal. Biochem.*, 72:248–254 (1976)).

EXAMPLE IX

Rat, Human Lung Membrane

Rat or human lung (3 gm) was prepared as a modification of Skidgel et al. (*Biochemical Pharmacology* 33: 3471 (1984)). Tissues were removed and placed in cold phosphate-saline (3×). Material was minced and homogenized in 20 volumes (w/v) of 0.5 mM tris HCl. 50 mM mannitol, pH 7.0. Calcium chloride was added to the homogenate to give a final concentration of 10 mM. The material was filtered through a guaze pad to remove loose connective tissue. Filtrate was spun in a Beckman centrifuge (3,000×g) for thirty minutes. The resultant supernatant fraction was spun in a Beckman L7-65 ultracentrifuge (43,000×g, 30 min) to spin down membranes. The centrifugation step was repeated on the membrane pellet fraction two additional times. The pellet was reconstituted in 4 ml of the tris mannitol buffer and stored at −70° C. Protein was determined by the method of Bradford.

EXAMPLE IX

Stability

Bradykinin antagonists were prepared at 1 mM concentration in a phosphate-buffered saline solution (phosphate saline, 2.6 mM $KH_2PO_4$, 10.42 mM $Na_2HPO_4$, 0.1454M NaCl, pH. 7.2). Aliquots (10 μl) of the compound were added to 90 μl of the tissue samples in Eppendorf tubes. Samples were incubated various time points at 37° C. At each time point protein was precipitated by addition of acetonitrile, acetonitrile made 0.1M HCl or 10% (v/v) trifluoroacetic acid in water (100 μl). Tubes were spun (14,000 rpm, 10 min) in an Eppendorf Model 5415C microcentrifuge. Samples were filtered and analyzed using reverse-phase HPLC ($C_{18}$ column 4.6×150 mm) and a 13.5% to 90% acetonitrile gradient in 0.1% TFA. Compound half-life was determined by analysis of raw data using ENZFIT application software (Elsevier).

[1]HPLC: Waters Model 712 Autosampler, Model 484 Variable Wavelength Detector, and Millipore Model 810 Application software.

TABLE III

Stability of Compounds CP-0298, B9812 & B9066 in Biological Fluids

| Compound | Half-Life (h) |
|---|---|
| (Rat kidney Brush Border) | |
| Bradykinin | 0.13 |
| CP-0298 | 0.020 |
| B9066 | >>6 |
| B9812 | >>6 |
| (Rat Lung Membranes) | |
| Bradykinin | 0.13 |
| CP-0298 | 0.085 |
| B9066 | >>6 |
| B9812 | >>6 |

We claim:

1. A bradykinin antagonist of the formula:

$$X-A^0-B^1-C^2-D^3-E^4-F^5-G^6-H^7-J^8-Z$$

wherein
- X is absent or is an aromatic, aliphatic, aromatic-aliphatic, alicyclic, heterocyclic or urethane-type acylating group, or at least one amino acid;
- $A^0$, $B^1$, $C^2$, $D^3$, and $E^4$ are basic or neutral aromatic, aliphatic, heterocyclic, or alicyclic amino acids or $A^0$ is absent;
- $G^6$ is an aromatic, aliphatic, heterocyclic, or alicyclic amino acid;
- $F^5$, $H^7$ and $J^8$ are aromatic, aliphatic, aliphatic heterocyclic, or alicyclic amino acids, provided that at least one of F, H and J is selected from Chg, Cpg, Igla, Iglb, Niga and Nigb of the D- or L- configuration, and
- Z is COOH.

2. The bradykinin antagonist peptide according to claim 1, wherein
- $A^0$ and $B^1$ are basic amino acids;
- $C^2$ is Pro;
- $D^3$ is Hyp;
- $E^4$ is Gly;
- $F^5$ is an Indanyl amino acid;
- $G^6$ is Ser;
- $H^7$ is a D-Indanyl amino acid; and
- $J^8$ is an Indanyl amino acid.

3. The bradykinin antagonist according to claim 1, wherein
- X is Aaa, Aca, Acetyl, Dhq, Nba, Tba, Cha, Gun or Cpa;
- $A^0$ is DArg, DLys, Arg or Lys;
- $B^1$ is DArg, DLys, Arg, Cys or Lys;
- $C^2$ is Pro, DMF, NMF, MPIV, Hyp, Azt, Dhp, Inip, Thz, or Pop;
- $D^3$ is Hyp, Pop, Niga, MPIV, Pro, Azt, Dhp, Inip, or Thz;
- $E^4$ is Iglb, Nigb, Ala, or Gly;
- $F^5$ is Igla, Ser($SO_4$), Niga, Nigb, Leu, Chg, Ile, Val, Alg, Oic, Pop, Nle, Cpg, Thi or DMF;
- $G^6$ is Ser, DIglb, HBQ, Cys, or Gly
- $H^7$ is DIgla, Iglb, Niga, Nigb, DLeu, DChg, DIle, DVal, DCpg, DOic, DPop, DNle, Tic, DTic or DDMF; and
- $J^8$ is Igla, Lys, Niga, Nigb, Leu, Chg, Ile, Val, Cpg, Oic, Pop, or Nle.

4. A bradykinin antagonist according to claim 3 wherein
- X is Gun or absent;
- $A^0$ is DArg or Lys;
- $B^1$ is Arg or Cys;
- $C^2$ is Pro;
- $D^3$ is Hyp;
- $E^4$ is Gly;
- $F^5$ is Igla, Iglb, Cpg or Thi;
- $G^6$ is Ser;
- $H^7$ is DIgla, DIglb, DCpg, Tic or DTic; and
- $J^8$ is Leu, Cpg or Oic.

5. The bradykinin antagonist according to claim 4, selected from
- DArg-Cys-Pro-Hyp-Gly-Cpg-Ser-DCpg-Cpg;
- DArg-Lys-Pro-Hyp-Gly-Cpg-Ser-DCpg-Cpg;
- DArg-Arg-Pro-Hyp-Gly-Cpg-Ser-Tic-Cpg;
- DArg-Arg-Pro-Hyp-Gly-Thi-Ser-Tic-Cpg;
- DArg-Arg-Pro-Hyp-Gly-Cpg-Ser-DTic-Cpg;
- DArg-Arg-Pro-Hyp-Gly-Thi-Ser-DTic-Cpg;
- DArg-Arg-Pro-Hyp-Gly-Cpg-Ser-DCpg-Cpg;
- DArg-Arg-Pro-Hyp-Gly-Igl-Ser-DIgl-Oic;
- Arg-Pro-Hyp-Gly-Igl-Ser-DIgl-Leu;
- DArg-Arg-Pro-Hyp-Gly-Igl-Ser-DIgl-Leu;
- Gun- DArg-Arg-Pro-Hyp-Gly-Igl-Ser-DIgl-Oic;
- DArg-Arg-Pro-Hyp-Gly-Thi-Ser-DIgl-Oic;
- Gun- DArg-Arg-Pro-Hyp-Gly-Thi-Ser-DIgl-Oic;
- DArg-Arg-Pro-Hyp-Gly-Igl-Ser-DTic-Cpg;
- Lys-Arg-Pro-Hyp-Gly-Igl-Ser-DTic-Cpg;
- Lys-Arg-Pro-Hyp-Gly-Igl-Ser-DIgl-Oic; and
- Lys- Lys-Arg-Pro-Hyp-Gly-Igl-Ser-DIgl-Oic.

6. The bradykinin antagonist according to claim 1, selected from
- Lys-Lys$^0$-Arg$^1$-Pro$^2$-Hyp$^3$-Gly$^4$-Iglb$^5$-Ser$^6$-DIglb$^7$-Oic$^8$; and
- Gun-DArg$^0$-Arg$^1$-Pro$^2$-Hyp$^3$-Gly$^4$-Thi$^5$-Ser$^6$-DIglb$^7$-Oic$^8$.

7. A method of treating acute or chronic inflammation comprising administering to a mammalian host in need of such treatment a therapeutic amount of the bradykinin antagonist according to claim 1.

8. A method of treating angiogenic diseases comprising administering to a mammalian host in need of such treatment a therapeutic amount of the bradykinin antagonist according to claim 1.

9. The according to claim 8 wherein the angiogenic disease is rheumatoid arthritis.

10. The according to claim 8 wherein the angiogenic disease is diabetic retinopathy.

11. The according to claim 8 wherein the angiogenic disease is cancer.

12. The bradykinin antagonist:
- Gun-Gly-Lys-Arg-Pro-Pro-Gly-Phe-Ser-Pro-Leu (SEQ ID NO:1).

* * * * *